United States Patent [19]

Hadary

[11] Patent Number: 4,630,623
[45] Date of Patent: Dec. 23, 1986

[54] TOOTHPICK HOLDER

[76] Inventor: Joseph Hadary, 5405 Linden Ct., Bethesda, Md. 20814

[21] Appl. No.: 521,259

[22] Filed: Aug. 8, 1983

Related U.S. Application Data

[63] Continuation-in-part of Ser. No. 476,555, Mar. 16, 1983.

[51] Int. Cl.⁴ .............................................. A61C 15/00
[52] U.S. Cl. ...................................................... 132/89
[58] Field of Search ............................... 132/89, 93, 91

[56] References Cited

U.S. PATENT DOCUMENTS

| | | | |
|---|---|---|---|
| 1,220,933 | 3/1917 | Bates | 433/143 |
| 2,527,857 | 10/1950 | Strachan | 132/93 X |
| 4,397,327 | 8/1983 | Hadary | 132/89 |

FOREIGN PATENT DOCUMENTS

| | | | |
|---|---|---|---|
| WO82/01126 | 4/1982 | Sweden | 132/89 |
| 191896 | 1/1923 | United Kingdom | 132/89 |

*Primary Examiner*—Gregory E. McNeill
*Attorney, Agent, or Firm*—Dennis H. Lambert

[57] ABSTRACT

A toothpick holder for holding toothpicks in different positions to facilitate access to different portions of the mouth. The holder includes a handle with a pair of arms thereon each having a toothpick receiving opening therein and oriented to position the toothpick received in one opening for gaining access to a first portion of the mouth and to position a toothpick received in the other opening for gaining access to a different portion of the mouth.

5 Claims, 6 Drawing Figures

TOOTHPICK HOLDER

BACKGROUND OF THE INVENTION

Cross Reference to Related Application

This application is a continuation-in-part of application Ser. No. 476,555 filed Mar. 16, 1983.

1. Field of the Invention

This invention relates to dental implements, and more particularly, to a toothpick holder for holding toothpicks in a plurality of different positions for easier access to different areas of the mouth.

2. Prior Art

It is well known by the dental profession that brushing does not always adequately clean the teeth, particularly in the areas between the teeth. Thus, flossing and other cleaning methods are recommended in conjunction with brushing. Moreover, the proper use of toothpicks is very beneficial in any oral hygiene program, and can be particularly effective in cleaning the spaces between the teeth.

However, except for a few attempts at developing a toothpick holder, people are generally limited to the use of wood or plastic toothpicks held in the user's hand. Accordingly, the use of a toothpick is only partially effective in cleaning the teeth, and those areas which are difficult to reach are usually not cleaned.

Examples of prior art toothpick holders are shown in U.S. Pat. Nos. 710,948, 1,291,282, 3,892,040 and those patents cited in parent application Ser. No. 476,555 filed Mar. 16, 1983.

U.S. Pat. No. 710,498 describes a quill-like member which is inserted through a shaped holder whereupon the quill-like member is curved to form a pick. U.S. Pat. No. 1,291,282 discloses a threaded holder having a pair of openings therein for receiving a toothpick in either of two different positions. U.S. Pat No. 3,892,040 discloses a holder having a threaded sleeve which is movable against a round toothpick to clamp the toothpick in position.

U.S. Pat. No. 3,471,929 discloses a dental implement in which a shaft 26 is held to a handle by a pin 8. A blade 30 is carried by the shaft for performing gum cutting operations.

None of the above patents teaches a toothpick holder capable of holding a pair of toothpicks in different orientations for gaining access to different areas of the mouth.

SUMMARY OF THE INVENTION

The present invention provides a toothpick holder which is easy to use and which comprises a handle with a pair of arms thereon, each having an opening therein for receiving and holding a toothpick. The arms and openings are arranged so that the toothpick held by one arm is oriented for gaining access to one portion of the mouth and the toothpick held in the other arm is oriented for gaining access to a different portion of the mouth.

There are three forms of the present invention, one of which has arms at opposite ends of an elongate handle defining a wide U-like shape, a second of which has arms at opposite ends of an elongate handle defining a Z-like shape, and a third of which has a T-shaped configuration with a pair of oppositely directed arms at one end of the "T". Each form of the invention has enlarged portions for engagement with the fingers or thumb of the user's hand to facilitate gripping of the holder.

PURPOSE OF THE INVENTION

It is a principal object of the present invention to provide a toothpick holder which is simple and economical in construction and which is easy to use.

Another object of the invention is to provide a toothpick holder which has a pair of arms each having an opening therein for receiving and gripping a toothpick, whereby two toothpicks are held by the holder in different orientations to facilitate access to different areas of the mouth.

BRIEF DESCRIPTION OF THE DRAWINGS

These and other objects and advantages of the invention will become apparent from the following detailed description and accompanying drawings, in which like reference characters refer to like parts throughout the several views, and wherein.

DESCRIPTION OF THE PREFERRED EMBODIMENTS

Figure 1:
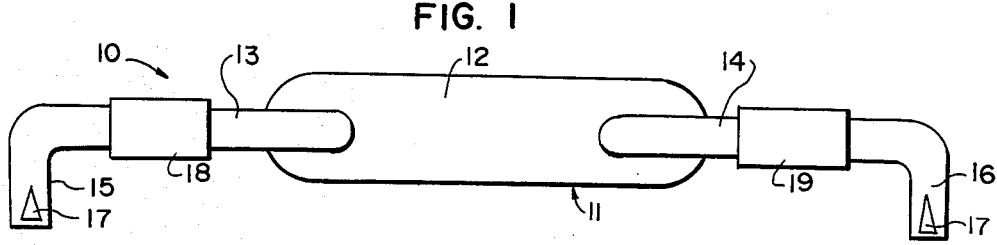
FIG. 1 is a front view in elevation of a first form of holder in accordance with the invention.
Figure 2:
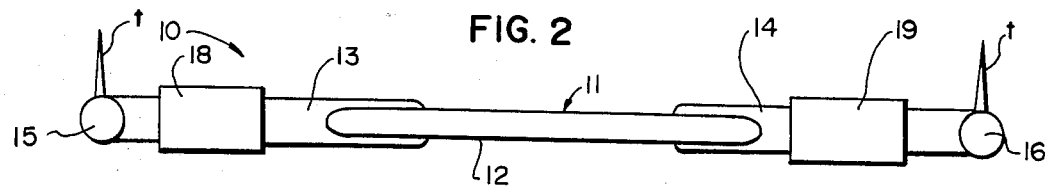
FIG. 2 is a top plan view of the holder of FIG. 1.

Referring now more particularly to the drawings, the first form of the invention is indicated generally at 10 in FIGS. 1 and 2, and comprises an elongate handle 11 having a relatively flat, wide midportion 12 extending over slightly more than ⅓ the total length of the handle.

A pair of coaxial, solid, cylindrical-shaped stems 13 and 14 project from opposite ends of the midportion 12, and short arms 15 and 16 project at a right angle from the outer ends of the stems 13 and 14, respectively. As seen best in FIG. 1, the arms 15 and 16 project in the same direction from the handle, so that the handle has a very wide U-shape when viewed in front elevation.

Each arm 15 and 16 has a triangularly shaped opening 17 therein, with the base of the openings adjacent the outer ends of the arms and the apex pointed toward the junction of the arms and stems.

In use, a soft toothpick, made of Bass wood or Balsa, for example, is inserted into one of the two openings and broken off as indicated in FIG. 2, thus orienting the toothpick in a position for gaining access to a first portion of the mouth. If it is desired to gain access to a different portion of the mouth, a toothpick is inserted into the other opening.

An enlarged polygonally shaped gripping portion 18 and 19, respectively, is provided on each of the stems between the ends thereof, against which the finger or thumb is rested during use to enhance control of the handle.

Figure 3:
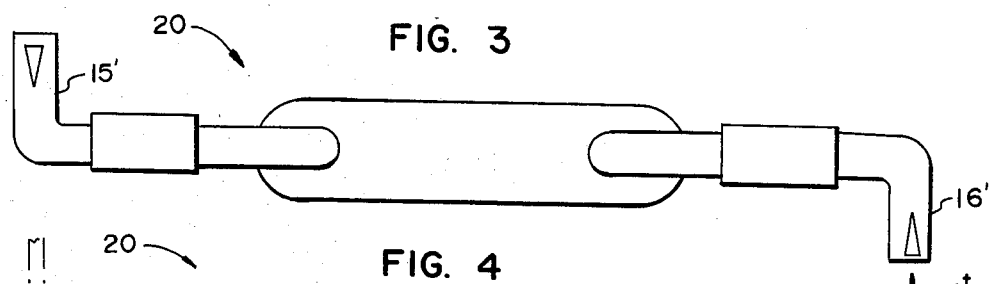
FIG. 3 is a front view in elevation of a second form of holder in accordance with the invention.
Figure 4:
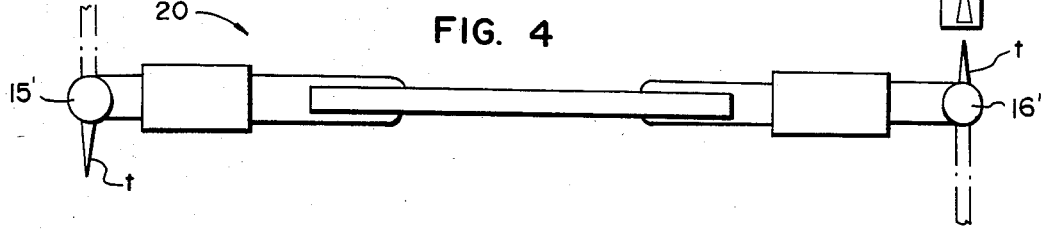
FIG. 4 is a top plan view of the holder of FIG. 3.

A second form of the invention is indicated generally at 20 in FIGS. 3 and 4 and is essentially the same as the form previously described except that the arms 15' and 16' at opposite ends of the handle project in opposite directions from the axis of the handle, defining a Z-like configuration, as seen best in FIG. 3. Further, the toothpicks "t" are inserted into their respective openings from opposite sides of the plane of the handle and broken off as shown in FIG. 4. Use of the holder is basically the same as that previously described.

Figure 5:
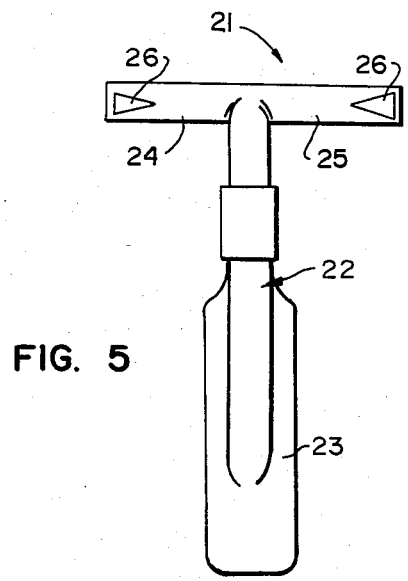
FIG. 5 is a front view in elevation of a third form of holder in accordance with the invention.
Figure 6:
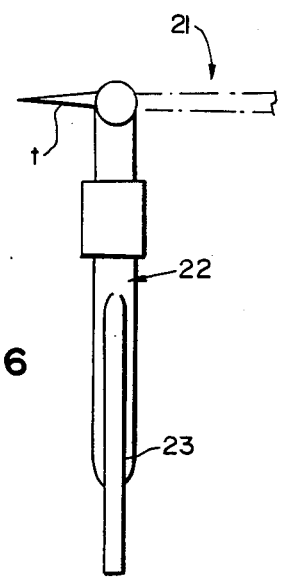
FIG. 6 is a side view in elevation of the holder of FIG. 5.

A third form of the invention is indicated generally at 21 in FIGS. 5 and 6, and in this form of the invention the holder comprises a "T"-shaped handle 22 with a flattened end portion 23 extending over most of the length of the handle, and a pair of oppositely directed arms 24 and 25 on the other end of the handle. Each arm has a triangularly shaped opening 26 therein, with the flat portion or base of the openings disposed adjacent the outer end of the respective arm and the apex of the openings pointing toward the middle.

In use, a toothpick may be inserted into a desired one of the openings and broken off, as before, whereby the holder may be oriented for gaining access to different parts of the mouth simply by inserting a toothpick into the appropriate opening.

The holders in accordance with the several forms of the invention disclosed herein may be made from any suitable material such as plastic, stainless steel or the like.

The relatively soft toothpicks are firmly gripped in the openings, and in practice, it has been observed that when the toothpicks get wet they swell, thus resulting in a firmer grip by the opening. The specific shape of the openings and the manner in which they grip the toothpicks are more fully described in copending application Ser. No. 476,555, filed Mar. 16, 1983.

While the holder has been described and shown in detail, it is obvious that the invention is not to be limited to the exact form disclosed, and that changes in detail and construction may be made therein within the scope of the invention, without departing from the spirit thereof.

Having thus set forth and disclosed the nature of this invention, what is claimed is:

1. A toothpick holder for holding toothpicks in different positions for gaining access to different portions of the mouth, comprising:
    an elongate, one-piece handle having portions of polygonal cross-sectional shape to facilitate gripping thereof;
    a pair of arms integral with the handle and each projecting therefrom at substantially a right angle to the axis of the handle; and
    each said arm having a free end with an opening therethrough, said openings each having a polygonal cross-sectional configuration adapted to grip and hold a toothpick inserted therein in a predetermined orientation, said openings being oriented so that a toothpick inserted into one of the openings is oriented in a first position for gaining access to a first portion of the mouth and a toothpick inserted into the other of the openings is oriented for gaining access to a different portion of the mouth.

2. A toothpick holder as claimed in claim 1, wherein: said arms are on opposite ends of the handle.

3. A toothpick holder as claimed in claim 2, wherein: one arm points in a first direction from the axis of the handle and the other arm points in the opposite direction.

4. A toothpick holder as claimed in claim 2, wherein: the arms point in the same direction from the axis of the handle.

5. A toothpick holder as claimed in claim 1, wherein: the handle is generally "T" shaped, said arms being on the same end of the handle and projecting in opposite directions therefrom.

* * * * *